(12) United States Patent
Roush

(10) Patent No.: US 8,454,614 B2
(45) Date of Patent: Jun. 4, 2013

(54) HYBRID FUSION/ARTHROPLASTY APPARATUS AND METHODS

(76) Inventor: Thomas F. Roush, West Palm Beach, FL (US)

(*) Notice: Subject to any disclaimer, the term of this patent is extended or adjusted under 35 U.S.C. 154(b) by 5 days.

(21) Appl. No.: 13/075,984

(22) Filed: Mar. 30, 2011

(65) Prior Publication Data

US 2011/0178561 A1    Jul. 21, 2011

Related U.S. Application Data

(63) Continuation of application No. 11/777,521, filed on Jul. 13, 2007, now Pat. No. 7,938,834.

(51) Int. Cl.
*A61F 2/46* (2006.01)

(52) U.S. Cl.
USPC ............................. 606/86 R; 606/90; 606/95

(58) Field of Classification Search
USPC ................ 606/60–63, 67, 73, 86 A, 86 R, 90, 606/95, 99, 204, 246, 279, 300–321; 623/17.11–17.16
See application file for complete search history.

(56) References Cited

U.S. PATENT DOCUMENTS

| | | | |
|---|---|---|---|
| 4,569,338 A | 2/1986 | Edwards | |
| 4,657,550 A | 4/1987 | Daher | |
| 5,034,011 A | 7/1991 | Howland | |
| 5,108,397 A | 4/1992 | White | |
| 5,147,294 A | 9/1992 | Smith et al. | |
| 5,242,444 A | 9/1993 | MacMillian | |
| 5,334,205 A | 8/1994 | Cain | |
| 5,458,641 A * | 10/1995 | Ramirez Jimenez | 623/17.11 |
| 5,643,264 A | 7/1997 | Sherman et al. | |
| 5,928,239 A | 7/1999 | Mirza | |
| 6,053,916 A | 4/2000 | Moore | |
| 6,635,059 B2 | 10/2003 | Randall et al. | |
| 2002/0087161 A1 | 7/2002 | Randall et al. | |
| 2005/0025765 A1 | 2/2005 | DiMauro et al. | |
| 2005/0152905 A1 | 7/2005 | Omoigui | |
| 2006/0030845 A1 | 2/2006 | Leung et al. | |
| 2006/0106376 A1 | 5/2006 | Godara et al. | |
| 2006/0200121 A1 | 9/2006 | Mowery | |
| 2006/0217705 A1 | 9/2006 | Godara et al. | |
| 2006/0259026 A1 | 11/2006 | Godara et al. | |
| 2007/0255408 A1* | 11/2007 | Castleman et al. | 623/17.11 |
| 2008/0243254 A1* | 10/2008 | Butler | 623/17.16 |
| 2009/0024174 A1 | 1/2009 | Stark | |

* cited by examiner

*Primary Examiner* — Eduardo C Robert
*Assistant Examiner* — Christina Negrellirodriguez
(74) *Attorney, Agent, or Firm* — Brinks Hofer Gilson & Lione

(57) ABSTRACT

The present embodiments relate to a joint treatment device for improved treatment of a diseased joint. The joint treatment device comprises first and second components, which are coupled to first and second bone portions, respectively, at the joint. The first component and the second component are configured to be coupled together in a first configuration to promote fusion of the joint, and further are configured to be coupled together in a second configuration to promote arthroplasty of the joint. Additionally, a screwdriver is disclosed that may advance the first and second component simultaneously or independently. Further, a joint distraction device is disclosed, which may be used to vary spacing between the first bone portion and the second bone portion at the joint.

16 Claims, 6 Drawing Sheets

HYBRID FUSION/ARTHROPLASTY APPARATUS AND METHODS

The present patent document is a continuation application that claims the benefit of priority under 35 U.S.C. §120 of U.S. patent application Ser. No. 11/777,521, filed Jul. 13, 2007 now U.S. Pat. No. 7,938,834, which is hereby incorporated by reference in its entirety.

TECHNICAL FIELD

The present embodiments relate generally to medical devices, and more particularly, to apparatus and methods that can be used in the implantation of medical devices to treat a variety of conditions.

BACKGROUND

Much of the human and animal population will experience pain emanating from joints or discs at some point in their lives. For example, pain may be located at or near the lumbosacral intervertebral disc, sacroiliac joint, tibiotalar joint, and subtalar joint. Diseases or disorders in any of these or other areas can cause debilitating pain as well as limited mobility in a patient.

There are many treatments for alleviating the pain emanating from joints or discs. In one field of therapy, surgical devices may be implanted at one or more locations to treat such painful conditions. For example, fusion devices may be positioned between vertebrae or within/across the sacroiliac, tibiotalar and subtalar joints to facilitate their fusion. Such devices are typically employed in conjunction with rods, screws, hooks, or plates that are also connected to neighboring bony elements. Problematically, due to a significant increase of surgical fusion technologies at joints neighboring the sacroiliac joint, tibiotalar joint, and subtalar joint, a degenerative process of these joints may occur because adjacent surgical fusions may accelerate neighboring joint degeneration. As a result, joints which rarely become diseased will become increasingly diseased. Moreover, many joints will require surgical treatment in the future due to an accelerated disease process.

Systems are also connected to these anatomic sites in the absence of fusion devices, so as to support or realign elements such as vertebrae. Such systems include non-fusion technologies such as arthroplasty/joint replacement of the intervertebral disc, tibiotalar and subtalar joints. No such motion-preserving technologies are believed to be known for the sacroiliac joint.

Disc nucleus implants are also known for receipt within the interior space of a damaged or otherwise ineffectual intervertebral disc. Many such devices that have been proposed are formed of hydrogels or elastomeric polymers, for absorbing impact and other forces occurring between the vertebrae.

While there are a wide array of implant devices, most have in common the need for relatively large surgical incisions for insertion, and many of the arthroplasty implants require a more traditional open surgery. Drawbacks in the application of these devices include invasive open procedures whereby the surgeon directly visualizes the joint and performs the surgery through sizable incisions that may lead to increased rates of early morbidity including wound complications.

Furthermore, the implants inserted for fusion and arthroplasty are inherently unrelated, necessitating a definite pre-surgical plan that sometimes may be difficult to predict. As a result, multiple implants must be present at the time of such surgery which often creates delays in preparing the proper implant, leading to longer surgeries and monetary waste since prepared implants and devices may be unused.

In view of the foregoing, there exists a need for synergistic medical devices to treat various joints and discs, such as the lumbosacral disc, the sacroiliac joint, the tibiotalar joint and the subtalar joints, in a more efficient and effective manner.

SUMMARY

The present embodiments relate to a joint treatment device for improved treatment of a diseased joint. In a first embodiment, the joint treatment device comprises first and second components, which are coupled to first and second bone portions at the joint, respectively. The first component and the second component are configured to be coupled together in a first configuration to promote fusion of the joint, and further are configured to be coupled together in a second configuration to promote arthroplasty of the joint.

In one embodiment, the first component has a generally cylindrical solid body that is adapted to be engaged with a first bone portion at the joint. The second component has a generally cylindrical body having a hollow interior region, wherein the generally cylindrical solid body of the first component is adapted to be selectively placed within the hollow interior region of the second component. The second component further is adapted to be engaged with a second bone portion at the joint.

In use, the joint treatment device may be used to promote either fusion or arthroplasty with relatively minor adjustments. For example, if fusion of the joint is desired, a fusion component may be inserted to mate with portions of the first and second components, thereby securing the components together to promote fusion of the joint. If arthroplasy of the joint is desired, then a different arthroplasy component may be inserted and coupled between the first and second components. The arthroplasty component may be disposed at least partially within the second component, but may comprise a protrusion adapted to rotate within a recess of the first component, thereby allowing rotation of the first and second components with respect to each other.

Advantageously, the physician does not need to decide whether to perform a fusion procedure or an arthroplasty procedure until after drilling a hole and directly observing the joint's articulation during surgery. When the decision is made, the same first and second components are still advanced and secured to their respective bone portions, however, either the fusion component or the arthroplasty component may be subsequently inserted to complete the procedure.

Additionally, the present embodiments provide a screwdriver that may be used to advance the first and second components simultaneously or independently. The screwdriver preferably comprises a first module, a second module and a handle that may be used modularly in at least two different configurations. In one configuration, the handle of the screwdriver is configured to directly releasably engage the first module to cause advancement of only the first component. In another configuration, the handle of the screwdriver is configured to directly releasably engage the second module to cause advancement of only the second component. In a still further configuration, the handle of the screwdriver is configured to directly releasably engage the second module, and the second module is further configured to directly releasably engage the first module, to thereby cause simultaneous advancement of the first component and the second component.

A joint distraction device is also disclosed, which may be used to vary the spacing between the first bone portion and the second bone portion at the joint. The joint distraction device may be used to vary the spacing prior to insertion of the first and second components of the joint treatment device.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patent's anatomy during a medical procedure.

Figure 1:
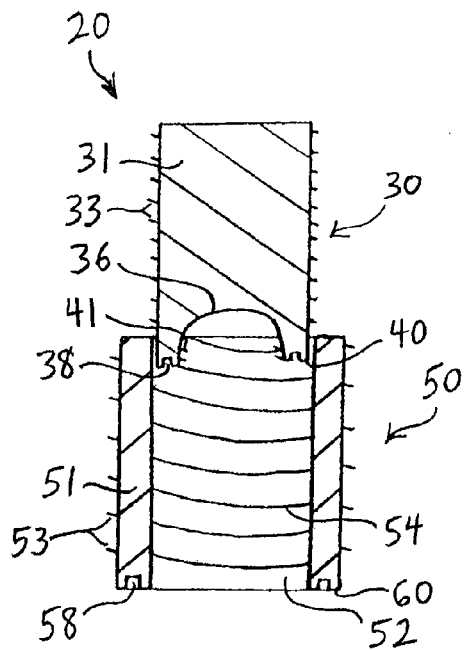
FIG. 1 is a side-sectional view illustrating first and second components of a joint treatment device.

Referring now to FIG. 1, a first embodiment of a joint treatment device is described. Joint treatment device 20 comprises first component 30, which may comprise a generally cylindrical solid body 31, and further comprises second component 50, which may comprise a generally cylindrical body 51 having a hollow interior region 52.

First component 30 preferably comprises external threading 33, which is adapted to engage a first bone portion to secure the first component 30 to the first bone portion, as will be explained in further detail below. Similarly, second component 50 preferably comprises external threading 53, which is adapted to engage a second bone portion to secure the second component 50 to the second bone portion.

Second component 50 may further comprise internal threading 54 formed in hollow interior region 52. The thread pitch of external threading 33 of first component 30 is identical to the thread pitch of internal threading 54 of second component 50, and therefore may be screwed in a proximal or distal direction to selectively link the two pieces together, as explained in further detail below.

In one embodiment, external threading 33 of first component 30 comprise a shorter thread pitch relative to external threading 53 of second component 50. The shorter thread pitch of external threading 33 is chosen to cause a distraction force across the anatomic articulation when used in conjunction with second component 50, as explained further below.

The distal end of first component 30 preferably is substantially flat, while the proximal end of first component 30 may comprise recess 36, as shown in FIG. 1. Recess 36, which preferably comprises a concave or dome-shape, serves various purposes. For example, if joint treatment device 20 is to be used as a fusion device, then internal threading 41 in recess 36 may engage a third component, such as fusion component 70 of FIG. 3, to help rigidly secure the first and second components 30 and 50 together. By contrast, if joint treatment device 20 is to be used as an arthroplasty device, then arthroplasty component 80 of FIG. 5 may be inserted into second component 50 and positioned to mate with recess 36 of first component 30, thereby providing a rotational interface between first and second components 30 and 50, as explained further below with respect to FIG. 6 and FIG. 12. It should be noted that internal threading 41 may be configured not to substantially interfere with rotation of arthroplasty component 80 when joint treatment device 20 is used as an arthroplasty device.

Recess 36 may be disposed centrally within cylindrical solid body 31, thereby forming outer ridge 40 at the proximal end surface of first component 30, as shown in FIG. 1. The proximal end of first component 30, formed by outer ridge 40, may comprise at least two recesses 38 formed therein, as shown in FIG. 1. As will be explained further below, recesses 38 may be adapted to releasably mate with screwdriver 100 of FIG. 7 to retract or advance first component 30.

Figure 2:
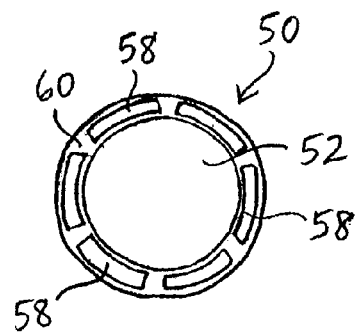
FIG. 2 is an end view showing the proximal end of the second component of FIG. 1.

Similarly, the proximal surface of second component 50 may form outer ridge 60 surrounding hollow interior region 52. Outer ridge 60 preferably comprises at least two recesses 58 disposed around its circumference, as shown in FIG. 2. Recesses 58 also may be adapted to releasably mate with screwdriver 100 of FIG. 7 below.

In a preferred embodiment, recesses 38 and 58 may comprise curvilinear cross-section or configuration, as illustratively depicted in FIG. 2. While six recesses 58 are depicted, it will be understood that greater or fewer may be employed. Moreover, in lieu of a curvilinear configuration, recesses 38 and 58 may comprise circular, square, rectangular, or other configurations.

As will be explained further below, recesses 38 and 58 of first and second components 30 and 50, respectively, are adapted to mate with corresponding protrusions of modular screwdriver 100 of FIG. 7. For example, protrusions 105 of screwdriver 100 (see FIG. 7) may comprise a curvilinear shape adapted to be disposed within corresponding recesses 38 of first component 30. Similarly, protrusions 115 of screwdriver 100 may comprise a curvilinear shape adapted to be disposed within corresponding recesses 58 of second component 50. Using this engagement technique, actuation of screwdriver 100 may cause first and second components 30 and 50 to be advanced and/or retracted to engage bone portions, as explained in further detail below.

Figure 3:
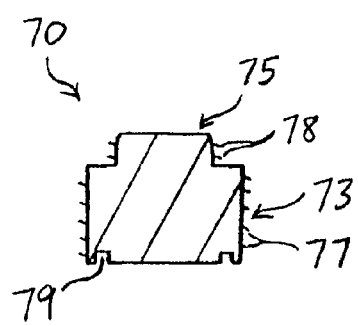
FIG. 3 is a side-sectional view illustrating a fusion component that may be used in conjunction with the apparatus of FIG. 1.
Figure 4:
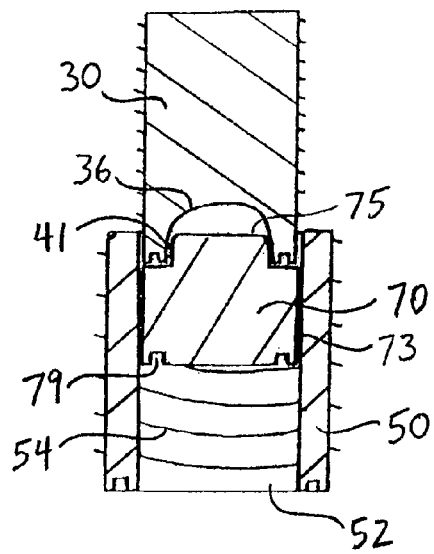
FIG. 4 is a side-sectional view illustrating the first and second components of FIG. 1 in a fusion configuration.

Referring now to FIGS. 3-4, when joint treatment device 20 is used as a fusion device, fusion component 70 may be employed to help rigidly secure first and second components 30 and 50 together. Fusion component 70 preferably comprises proximal portion 73 and distal portion 75. Proximal portion 73 comprises external threading 77, which is configured to mate with internal threading 54 of second component 50. Distal portion 75 comprises external threading 78, which is configured to mate with the internal threading 41 of first component 30 (see FIG. 1). Distal portion 75 preferably comprises a reduced outer diameter relative to proximal portion 73, as shown in FIG. 3, thereby allowing distal portion 75 to be at least partially disposed within recess 36 of first component 30 in the fusion configuration, as shown in FIG. 4. At least one recess 79, preferably provided in accordance with recesses 58 of FIG. 2, may be disposed in the proximal surface of fusion component 70 and configured to mate with a portion of screwdriver 100, thereby allowing advancement and retraction of fusion component 70.

Figure 5:
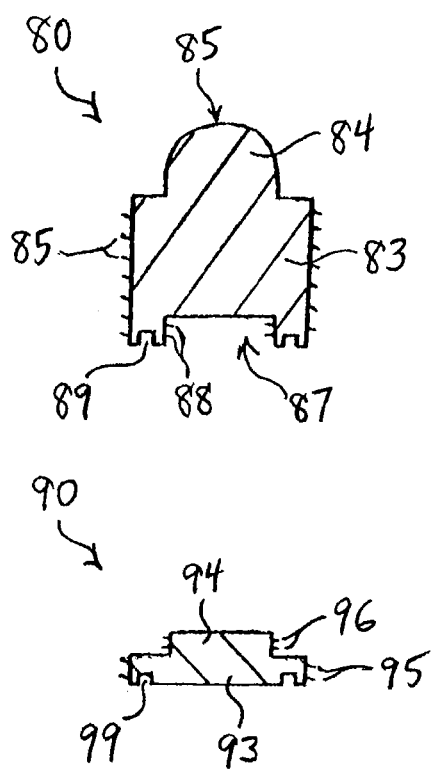
FIG. 5 is a side-sectional view illustrating an arthroplasty component and a locking cap that may be used in conjunction with the apparatus of FIG. 1.
Figure 6:
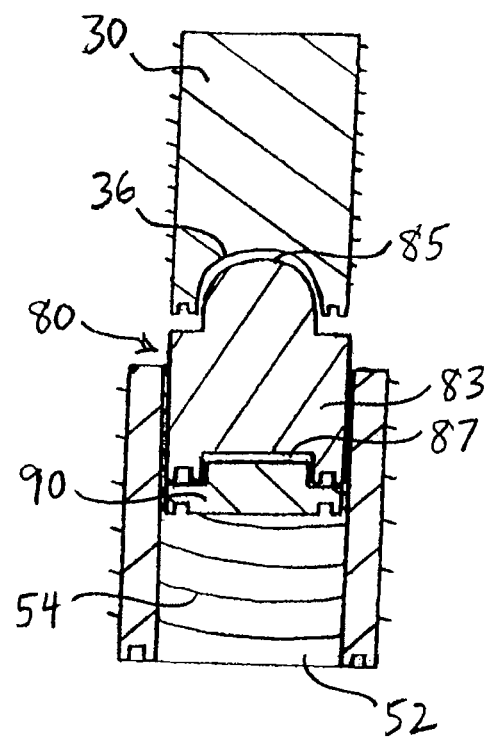
FIG. 6 is a side-sectional view illustrating the first and second components of FIG. 1 in an arthroplasty configuration.

Referring now to FIGS. 5-6, arthroplasty component 80 and locking cap 90 may be employed to couple first and second components 30 and 50 together when joint treatment device 20 is used as an arthroplasty device. Arthroplasty component 80 comprises proximal portion 83 and distal portion 84. Proximal portion 83 comprises external threading 85, which is configured to mate with internal threading 54 of second component 50, as shown in FIG. 6. Distal portion 84 comprises protrusion 85, which may comprise a convex or dome shape, as shown in FIG. 5. Protrusion 85 is configured to rotatably engage recess 36 of first component 30 in the arthroplasty configuration, as shown in FIG. 6 and explained further below. In an alternative embodiment, however, a protrusion may be formed in the proximal end of first component 30, and a corresponding recess may be formed in a distal surface of arthroplasty component 80, which represents an inversion of the mating arthroplasty features and may be desirable in some anatomic instances.

Referring still to FIG. 5, proximal portion 83 of arthroplasty component 80 also may comprise recess 87 having internal threading 88. Locking cap 90 having proximal and distal regions 93 and 94 may be used to secure arthroplasty component 80 to second component 50. In use, external threading 96 of distal region 94 may engage internal threading 88 of recess 87 of arthroplasty component 80, while external threading 95 of proximal region 93 may engage internal threading 54 of second component 50, as shown in FIG. 6. Locking cap 90 therefore provides a secure interface between arthroplasty component 80 and second component 50, thereby stabilizing the arthroplasty component during use. Further, locking cap 90 may be sized to cover at least a portion of internal threading 54 of second component 50 during use.

At least one recess 89, preferably provided in accordance with recesses 58 of FIG. 2, may be disposed in the proximal surface of arthroplasty component 80 and configured to mate with a portion of screwdriver 100, thereby allowing advancement and retraction of arthroplasty component 80. Similarly, at least one recess 99 may be disposed in the proximal surface of locking cap 90 to permit advancement and retraction of the locking cap using screwdriver 100, as explained below with respect to FIG. 7.

Figure 7:
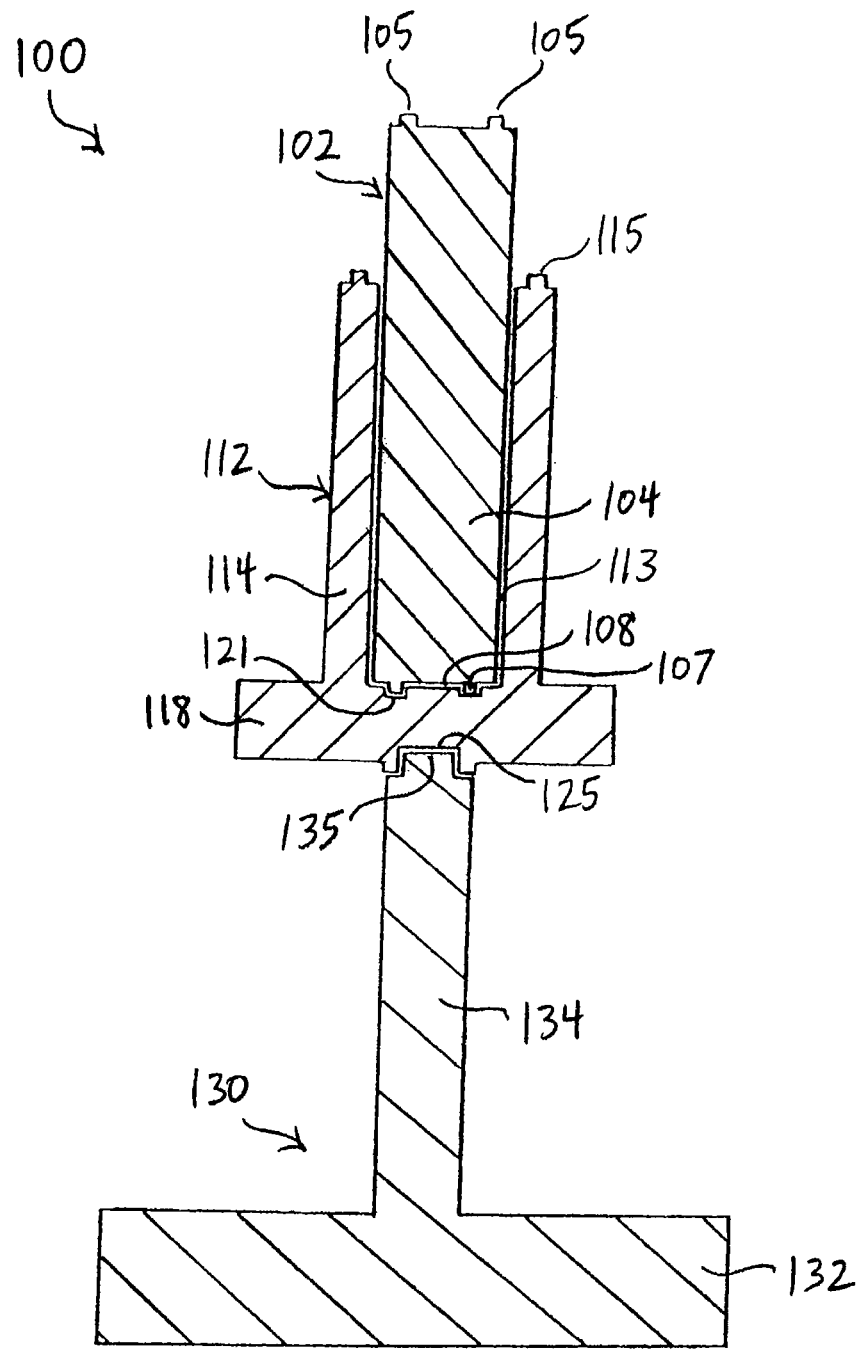
FIG. 7 is a side-sectional view of a screwdriver that may be used in conjunction with various components of FIGS. 1-6.

Referring now to FIG. 7, further features of screwdriver 100 are described. Screwdriver 100 preferably comprises a plurality of modular components that are designed to advance both first and second components 30 and 50 simultaneously or independently, depending upon the desired application.

In one embodiment, screwdriver 100 comprises first module 102, second module 112, and handle 130. First module 102 comprises a substantially cylindrical body member 104 having proximal and distal regions. The distal region of first module 102 comprises one or more protrusions 105, which as noted above, may be sized to matingly engage corresponding recesses 38 of first component 30. Protrusions 105 further are sized to engage recesses 79 of fusion component 70, recesses 89 of arthroplasty component 80, and recesses 90 of locking cap 90 to effect advancement or retraction of each component.

Second module 112 of screwdriver 100 comprises a body portion 114 having a hollow interior 113, which is adapted to receive at least a portion of cylindrical body member 104 of first module 102, as shown in FIG. 7. A distal region of second module 112 comprises one or more protrusions 115, which may be sized to matingly engage corresponding recesses 58 of second component 50. A proximal region of second module 112 comprises connecting portion 118 having at least one distal recess 121 and at least one proximal recess 125, as shown in FIG. 7.

Handle 130 may comprise any suitable shape adapted to be grasped by a human hand. In the embodiment of FIG. 7, handle 130 comprises a generally longitudinal portion 134 and a generally laterally-extending portion 132. The distal end of handle 130 comprises at least one protrusion 135, which is adapted to selectively engage either recess 108 of first module 102 or recess 125 of second module 112.

In use, handle 130 may be used in conjunction with first module 102 and/or second module 112. If it becomes desirable to engage only recesses 38 of first component 30 (see FIG. 1), then second module 112 may be omitted and first module 102 may be coupled directly to handle 130, for example, by employing a snap-fit connection between recess 108 and protrusion 135 of handle 130. If it becomes desirable to engage only recesses 58 of second component 50 (see FIG. 1), then first module 102 may be omitted and second module 112 may be coupled directly to handle 130, for example, by employing a snap-fit connection between recess 125 and protrusion 135 of handle 130.

If it becomes desirable to simultaneously advance or retract both first and second components 30 and 50, then both first and second modules 102 and 112 are used in conjunction with handle 130 as shown in FIG. 7. Specifically, at least a portion of cylindrical body member 104 of first module 102 is positioned within hollow interior 113 of second module 112. First and second modules 102 and 112 then may be securely coupled together by coupling protrusions 107 of first component 112 within corresponding recesses 121 of second component 112, e.g., using a snap-fit connection. Second module 112 further is coupled directly to handle 130, for example, by employing a snap-fit connection between recess 125 and protrusion 135 of handle 130. In the configuration of FIG. 7, protrusions 105 and 115 may simultaneously engage recesses 38 and 58, respectively, to enable simultaneous distal advancement or proximal retraction of first and second components 30 and 50.

Figure 8:
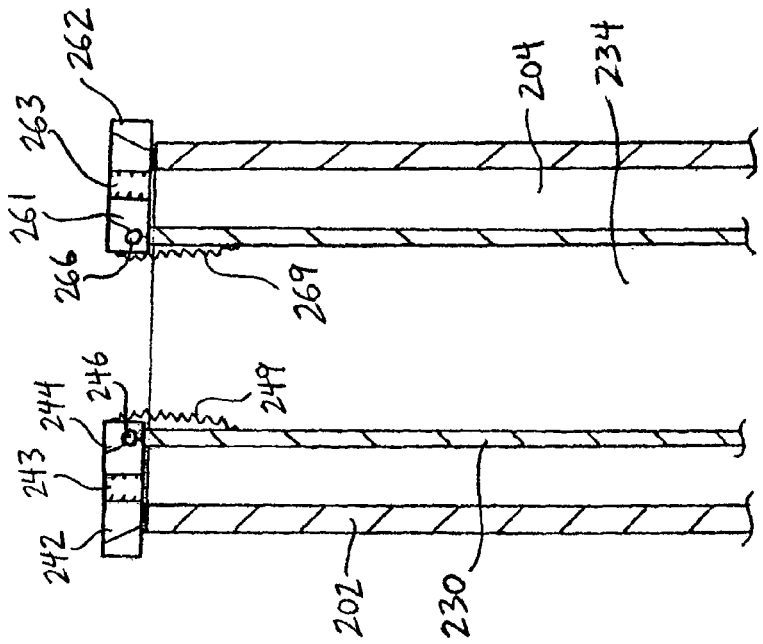
FIG. 8 is a side-sectional view of a joint distraction device in a delivery configuration.
Figure 9:
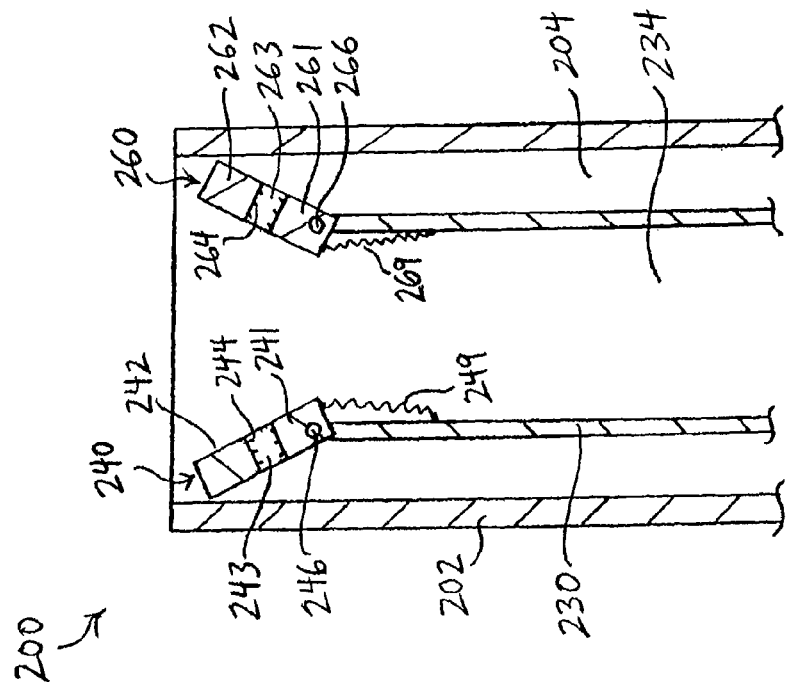
FIG. 9 is a side-sectional view of the joint distraction device of FIG. 8 in a deployed configuration.
Figure 10:
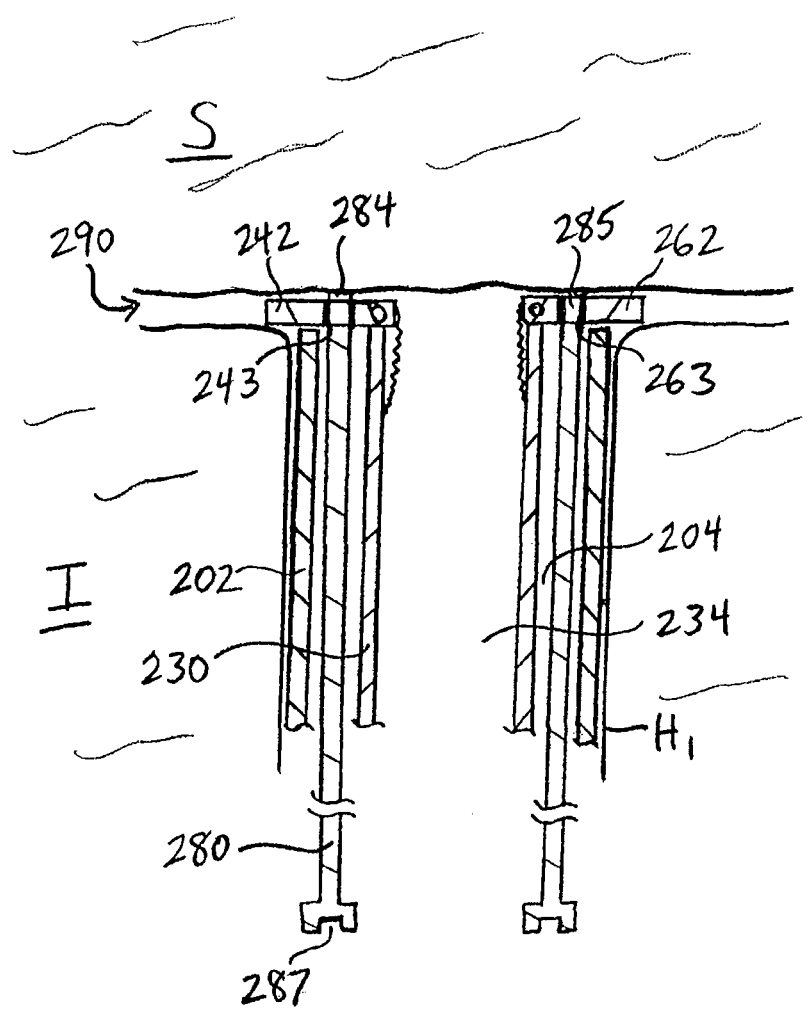
FIG. 10 is a side-sectional view of the joint distraction device of FIGS. 8-9 being used to distract a sacroiliac joint.

Referring now to FIGS. 8-10, joint distraction device 200 may be employed to prepare a joint location prior to implantation of joint treatment device 20, for example, by varying a spacing distance between bone portions at the joint. Joint distraction device 200 preferably comprises outer tube 202 and inner tube 230, as shown in FIGS. 8-9. Inner tube 230 comprises an outer diameter adapted to be advanced within lumen 204 of outer tube 202, as depicted in FIGS. 8-9.

In one embodiment, at least one spacing element is coupled to a distal end of inner tube 230. For example, first and second spacing elements 240 and 260 may be disposed approximately 180 degrees apart about the circumference of inner tube 230. In a preferred embodiment, first spacing element 240 comprises inner portion 241, outer portion 242, and an aperture 243 disposed therebetween, as shown in FIG. 8. Similarly, second spacing element 260 comprises inner portion 261, outer portion 262, and an aperture 263 disposed therebetween.

First and second spacing elements 240 and 260 may be coupled to inner tube 230 via hinge elements 246 and 266, respectively, as shown in FIGS. 8-9. Spring member 249 may be coupled between inner tube 230 and first spacing element 240, while spring member 269 may be coupled between inner tube 230 and second spacing element 260. The spring members function to bias first and second spacing elements 240 and 260 in radially outward directions, as shown in FIG. 9.

Referring now to FIG. 10, an exemplary use of joint distraction device 200 to vary spacing 290 at the articulation between ilium I and sacrum S at the sacroiliac joint is shown. In a first step, hole $H_1$ having a diameter slightly greater that an outer diameter of outer tube 202 is drilled into ilium I, as shown in FIG. 10. Outer tube 202 then is advanced through hole $H_1$ to a location just proximal to the articulation between ilium I and sacrum S. In a next step, inner tube 230 is advanced within lumen 204 of outer tube 202. During advancement, first and second spacing elements 240 and 260 may be radially restrained by outer tube 202, as shown in FIG. 8. When first and second spacing elements 240 and 260 are advanced beyond the distal end of outer tube 202, they expand radially due to the spring force provided by spring members 249 and 269, respectively, as shown in FIGS. 9-10.

At this time, outer portions 242 and 262 of first and second spacing elements 240 and 260, respectively, may become at least partially wedged within the articulation between ilium I and sacrum S, as shown in FIG. 10. Apertures 243 and 263 become aligned in a direction substantially parallel to the longitudinal axes of inner tube 230 and outer tube 202, and further, the apertures are disposed at locations between inner tube 230 and outer tube 202, as shown in FIGS. 9-10.

In a next step, at least one distracting screw may be advanced to vary spacing 290 between ilium I and sacrum S. In a preferred embodiment, the distracting screw comprises at least one elongated element 280 having proximal and distal ends. The distal end of each elongated element 280 comprises a threaded portion adapted to mate within internal threading 244 and 264 of apertures 243 and 263, respectively (see FIG. 8). The proximal end of each elongated element 280 preferably comprises at least one recess 287, which is adapted to releasably mate with a corresponding protrusion of screwdriver 100. Therefore, screwdriver 100 may effect advancement and retraction of elongated element 280.

In use, distal advancement of elongated element 280 relative to first and second spacing elements 240 and 260 will vary spacing 290 between ilium I and sacrum S, as depicted in FIG. 10. For example, if a surgeon wishes to perform an arthroplasty procedure after observing the joint articulation, additional spacing 290' may be provided at the articulation, as depicted in FIG. 12.

Advantageously, by providing at least two elongated elements 280, the distraction at the articulation is carried out over at least two columns. Working space is provided within lumen 234 of inner tube 230, as shown in FIG. 10. If desired, a series of cutters, curettes or any other device for the purposes of cleaning, rinsing, or removing joint components may then be introduced with the articulation under tension. For example, the removal of non-bony material, e.g., cartilage, fibrous tissue and synovial tissues, may be performed through lumen 234. Such substances produced may be extracted by a number of modalities, such as suction devices.

Therefore, regardless of whether joint treatment device 20 is to be used as a fusion or arthroplasty device, hole $H_1$ is drilled into ilium I and the articulation may be cleaned, rinsed and observed to determine which application is best. It should be noted that both first and second components 30 and 50 will subsequently be employed regardless of whether fusion or arthroplasy is chosen, as explained further in FIGS. 11-12 below.

Figure 12:
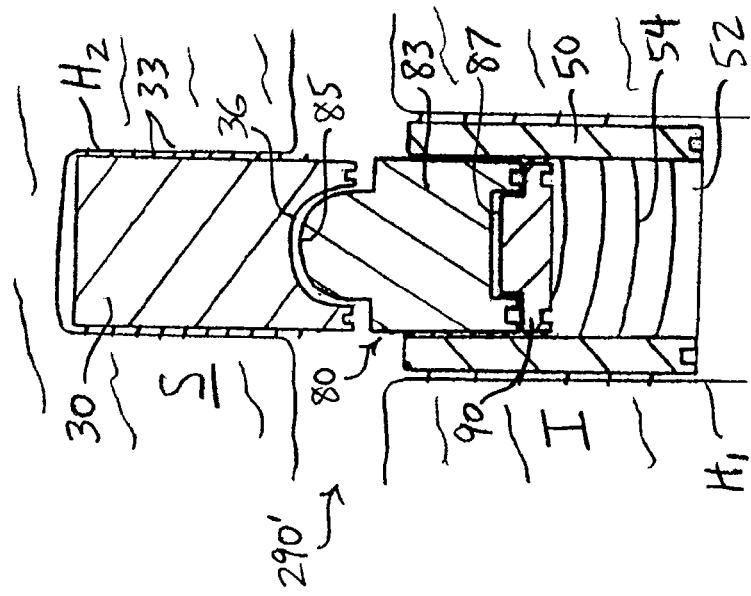
FIG. 12 is a side-sectional view depicting the joint treatment device being used to promote arthroplasty at a sacroiliac joint.
Figure 11:
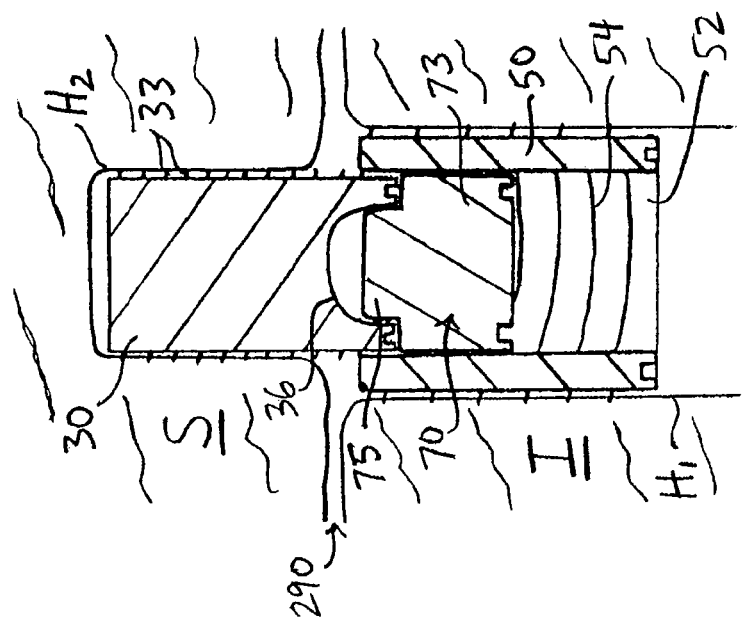
FIG. 11 is a side-sectional view depicting the joint treatment device being used to promote fusion at a sacroiliac joint.

Referring now to FIGS. 11-12, joint treatment device 20 is shown in a fusion configuration and in an arthroplasty configuration, respectively. For illustrative purposes, the procedure is shown performed between ilium I and sacrum S at the sacroiliac joint. As will be explained further below, the fusion or arthroplasy procedure may be performed at various other joints.

As noted above, after drilling hole $H_1$ into ilium I, and cleaning, rinsing, or removing joint components using joint distraction device 200, a physician then may decide whether to use joint treatment device 20 as a fusion or arthroplasty device. If fusion of the joint is desired, then joint distraction device 200 may remain in place, as shown in FIG. 10, and a bone graft with or without a bone-forming protein may be provided into the articulation through lumen 234. In a next step, hole $H_2$ may be drilled into sacrum S in a cannulated fashion, and joint distraction device 200 may be subsequently removed, as shown in FIG. 11.

Holes $H_1$ and $H_2$ are sized to receive second and first components 50 and 30 of joint treatment device 20, respectively. Therefore, first component 30 is advanced and secured within hole $H_2$ of sacrum S, while second component 50 is advanced and secured within hole $H_1$ of ilium I, as shown in FIGS. 11-12. As noted above, screwdriver 100 of FIG. 7 may be used to advance and secure first and second components 30 and 50 at the joint articulation. Moreover, first and second components 30 and 50 may be advanced simultaneously, or one at a time, as explained above with respect to FIG. 7.

In a preferred method, first and second components 30 and 50 are at least partially overlapped in a nested position, then simultaneously inserted into their respective holes $H_2$ and $H_1$ using screwdriver 100. Subsequently, second module 112 of screwdriver 100 may be removed, first module 102 of screwdriver 100 may be coupled directly to handle 130, and first component 30 then may be independently repositioned with respect to second component 50 if needed.

Once a physician has secured first and second components 30 and 50 within holes $H_2$ and $H_1$, if fusion of the sacroiliac joint has been selected, then fusion component 70 is advanced distally through hollow interior region 52 of second component 50, for example, using screwdriver 100. Fusion component 70 is advanced until external threading 78 mates with internal threading 41 of first component 30. At this time, fusion component 70 is securely coupled to both first and second components 30 and 50, which in turn promotes fusion between sacrum S and ilium I, as shown in FIG. 11.

During the fusion procedure, the sacroiliac joint may be viewed by biplanar x-ray. The biplanar x-ray may help image major neural and vascular structures in close proximity to the surgical field, which should be avoided. The additional information afforded by biplanar x-ray may significantly enhance the safety of the surgical procedure.

If arthroplasty of the sacroiliac joint has been selected, arthroplasty component 80 alternatively may be advanced distally through hollow interior region 52 of second component 50, for example, using screwdriver 100, until protrusion 85 engages recess 36 of first component 30. At this time, arthroplasty component 80 permits angular rotation between sacrum S and ilium I, as depicted in FIG. 12. If desired, first and second components 30 and 50 may be advanced separately or together and positioned in a spaced apart fashion, as shown in FIG. 12. This articulation allows for angular and rotational motion in the physiologic directions required by the anatomic site of implantation.

Therefore, joint treatment device 20 advantageously can function as promoting either fusion or arthroplasty with relatively minor adjustments, e.g., by selecting to insert either fusion component 70 or arthroplasty component 80 at the time of the operation. The relatively easy conversion between these two hybrid functions may be particularly attractive to a surgeon who may be unsure of the most appropriate application until he or she observes variables such as the bone quality/density, elasticity of the tissues surrounding the joint, and patient-specific anatomic features during the surgery.

Furthermore, when the choice of fusion or arthroplasty requires additional intraoperative data, the device and technique described allows the surgeon to make the selection with the newly acquired data and proceed without wasting time or resources which would otherwise be required when changing ultimate plans intraoperatively. This is particularly the case in the sacroiliac and subtalar joints, when the amount of distraction afforded by the articulation and the bone quality are critical variables when deciding between fusion and arthroplasty.

Additionally, since a substantial portion of the fusion or arthroplasty procedure is identical, the implantation of joint treatment device 20 allows for easier surgical perfection of the technique due to repetition, which is an important feature when introducing a new technology and may improve patient outcome. Moreover, as explained in further detail below, joint treatment device 20 may be inserted in a minimally invasive fashion across various articulations, including but not limited to the lumbosacral intervertebral disc, sacroiliac, tibiotalar and subtalar joints, thereby enhancing repetition and accelerating learning how to use the device.

It will be noted that procedures using joint treatment device 20 may be performed on individuals having normal, healthy bone. Alternatively, in some cases, joint treatment device 20 may be used with individuals having diseased or otherwise abnormal bone. When the condition is osteoporosis, the osteoporosis can be due to a number of conditions, e.g., age-related osteoporosis, post-menopausal osteoporosis, juvenile osteoporosis, Cushing's syndrome osteoporosis, multiple myeloma osteoporosis, leukemia osteoporosis, Turner's syndrome osteoporosis, alcohol osteoporosis, chronic liver disease osteoporosis, glucocorticoid-induced osteoporosis, chronic inflammatory disease induced osteoporosis and disuse osteoporosis. When used in such situations, bone cement with or without an osteogenic material may be beneficial to be placed in the established cavities of holes $H_1$ and/or $H_2$ prior to insertion of joint treatment device 20.

Further, the various surfaces of joint treatment device 20 may be coated with a number of substances to promote bone ingrowth or ongrowth. Such substances may be sprayed on or otherwise attached to one or more components of joint treatment device 20. Such substances include, but are not limited to, hydroxyapatite, tantalum, plasma-spray, or other biologic substances to promote regional osteogenesis for the purpose of improved attachment of the bone-device interface.

It should be noted that joint treatment device 20 also may be used for diagnoses of post-traumatic degenerative processes. This may be accompanied by adjacent degeneration, arthritis, or other complications, and joint treatment device 20 may be used to treat such conditions.

Finally, in other embodiments, surgical kits may be provided that are useful in the performance of the methods described hereinabove. Thus, in certain embodiments, the surgical kits may include a joint treatment device 20 that is configured for implantation, additional devices to specifically carry out the preparation of the bone channels, such as joint distraction device 200, and the specific osteoinductive or osteoconductive materials to promote fusion, if that is the intended result. The kit also may include screwdriver 100 to facilitate manipulation of the various components of joint treatment device 20. In addition, devices to properly clean out the specific joint spaces for a given procedure may be included. The medical device, delivery device, and bone-strengthening substance may, as examples, include any combination of those elements described herein.

The exemplary application of the devices, techniques and methods introduced above will now be described for four particular anatomic regions:

Sacroiliac Joint

Indications for implantation of joint treatment device 20 into the sacroiliac joint may include the results of a trial of diagnostic and therapeutic injection treatments. Injection of a variety of substances are possible. The user can choose between any anti-inflammatory substances, specifically substances such as anti-tumor necrosis factor (such as, but not limited to, etanercept, infliximab and adalimumab) and anti-interleukin compounds, protease and/or metabolic inhibitors, such as, but not limited to, those which inhibit glyceraldehyde-3-phosphate dehydrogenase such as, but not limited to, monosodium iodoacetate, and viscosupplementation such as, but not limited to hyaluronic acid type compounds. Additional injection of synthetic substance or colloid substance may be entertained, or any other substance that would effect a general stabilization and shock-absorption of the articulation.

Furthermore, the pathologic endpoint of the majority of diseases afflicting the sacroiliac joint includes the laxity of the joint itself. One of the benefits of joint treatment device 20 and joint distraction device 200 is the ability to apply distraction across the joint which stabilizes the joint due to tightening of the patient's existing ligaments which may have become lax.

With the option of using biplanar fluoroscopy, two simultaneous images representing a true anteroposterior and inlet view of the sacroiliac joint may be achieved. The true anteroposterior view would be that view obtained when the beam of the x-ray machine is angled to tangentially visualize the articular surface of the sacroiliac joint. An incision is placed to allow perpendicular access to the sacroiliac joint from an entry point in the ilium at the level corresponding to the junction of the superior and inferior cartilaginous limbs of the sacroiliac joint(s). Dissection is then done through the gluteus maximus muscle to the ilium. A sharp trocar (i.e. Jamshidi) is then placed on the ilium in a variable position to correspond to the junction of the superior and inferior cartilaginous limbs of the sacroiliac joint. This point is usually approximately 2 cm superior to the superiormost aspect of the sciatic notch. This point, however, is variable in patients and should be determined by fluoroscopy with or without injection of contrast into the sacroiliac joint. Once established, the sharp trocar (i.e. Jamshidi) is malleted into place across the mid-portion of the sacroiliac joint and into the corresponding sacrum, usually coming to rest medially between the superior 2 sacral foramina. At that time, sequential cannulated drilling is accomplished of the ilium side of the articulation, to reach a diameter approximately equivalent to an outer surface of second component 50. Joint distraction device 200 optionally may be introduced and deployed and the cartilaginous surface and any additional debris is mobilized and sucked out of the joint. Following this process, the decision is officially made to perform either a fusion or arthroplasty procedure, as explained above.

In a still further aspect, improved fixation of the lateral alar bone of the sacrum, which is often of a weak consistency, may be achieved by applying cement around the sacral portion of the device through the formed sacral channel. This allows an improved fixation into the sacral bone in situations where the bone density or stability is compromised, including but not limited to such situations as fracture, osteopenia, or osteoporosis. Though most likely employed for the sacrum, cement or other adhesives may also be applied to any other bones whether or not fixation of the implant is in question.

Lumbosacral Disc

The device when implanted across the lumbosacral disc is to be used as a prosthetic articulation arthroplasty device primarily, with the decision to use as a fusion device only in remote, intraoperative circumstances where arthroplasty is found to be unsafe or impossible.

In this procedure, a bony channel may be created perpendicular to the lumbosacral disc in its central portion. Joint distraction device 200 may be inserted and used through this bony channel. The optimal amount of distraction may be noted during this portion of the procedure. Following the removal of the distraction device, the joint treatment device 20 may be placed through the same bony channels across the disc space, with the attempt to recreate an optimal amount of distraction as visualized fluoroscopically. The joint treatment device 20 is then converted to the arthroplasty device as noted above.

Subtalar Joint

Indications for such implantation may include a trial of diagnostic and therapeutic treatments. Injection of a variety of substances are possible. The user can choose between any anti-inflammatory substances, specifically substances such as anti-tumor necrosis factor (such as, but not limited to, etanercept, infliximab and adalimumab) and anti-interleukin compounds, protease and/or metabolic inhibitors, such as, but not limited to, those which inhibit glyceraldehyde-3-phosphate dehydrogenase such as, but not limited to, monosodium iodoacetate, and viscosupplementation such as, but not limited to hyaluronic acid type compounds Using uniplanar fluoroscopy, a small, tissue-sparing incision may be placed on the plantar surface of the foot, anterior to the calcaneal tuberosity, to approach the joint at a right angle to the articular surface. The remainder of the procedure is the same technical exercise as that mentioned for the other anatomic regions, with the identical option of arthroplasty or fusion. In this instance, the larger bony channel is within the calcaneus, with the smaller bony channel being within the talus.

Tibiotalar Joint

Indications for such implantation would include a trial of diagnostic and therapeutic treatments. Injection of a variety of substances are possible. The user can choose between any of the various substances noted above with respect to the discussion of the subtalar joint.

The tibiotalar joint is approached by drilling through the subtalar joint as noted above, and reaching the tibiotalar joint in a perpendicular fashion to the plane of the joint. Most often this would require a concomitant procedure if the subtalar joint was functioning properly prior to the insertion of the implant in the tibiotalar joint. In this instance, the larger bony channel is within both the calcaneus and talus, with the smaller bony channel being within the tibia.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

What is claimed is:

1. Apparatus suitable for treating a medical condition, the apparatus comprising:
   a first component having proximal and distal ends and a generally cylindrical solid body that is engaged with a first bone portion at a joint; and
   a second component having proximal and distal ends, the second component comprising a generally cylindrical body having a hollow interior region, wherein the generally cylindrical solid body of the first component is adapted to be selectively placed within the hollow interior region of the second component, and the second component is adapted to be engaged with a second bone portion at the joint,
   wherein the first component and the second component are configured to be coupled together in a first configuration to promote fusion of the joint, and the first component and the second component are further configured to be coupled together in a second configuration to promote arthroplasty of the joint,
   wherein the second component comprises external threading adapted to securely engage the second bone portion, and further comprises internal threading adapted to releasably engage external threading disposed on at least a portion of the first component.

2. The apparatus of claim 1 wherein the proximal end of the first component further comprises a recess.

3. The apparatus of claim 2 further comprising a fusion component having a first portion comprising a substantially cylindrical body having external threading configured to mate with internal threading of the second component, and further comprising a second portion comprising external threading configured to mate with internal threading of the recess of the first component to promote fusion of the joint.

4. The apparatus of claim 2 further comprising an arthroplasty component having a first portion comprising a substantially cylindrical body comprising external threading configured to mate with internal threading of the second component, and further comprising a second portion comprising a protrusion configured to rotatably engage the recess of the first component to promote arthroplasty of the joint.

5. The apparatus of claim 4 wherein the protrusion comprises a dome shape.

6. The apparatus of claim 1 wherein the proximal end of the first component and the proximal end of the second component each comprise at least one recess adapted to engage a portion of a screwdriver to enable advancement of the first and second components.

7. The apparatus of claim 1 further comprising a joint distraction device configured to selectively vary spacing between the first bone portion and the second bone portion at the joint.

8. The apparatus of claim 1 wherein the first component and the second component are allowed to rotate relative to each other in the second configuration.

9. The apparatus of claim 1 wherein the generally cylindrical solid body of the first component is disposed within a pre-formed hole of the first bone portion.

10. The apparatus of claim 1 wherein the first component can rotate at acute angles with respect to a longitudinal axis defined by an elongate orientation of the second component.

11. A method suitable for treating a medical condition, the method comprising:
   engaging a first component having proximal and distal ends with a first bone portion at a joint, where the first component is a generally cylindrical solid body;
   engaging a second component having proximal and distal ends with a second bone portion at the joint;
   coupling the first and second components together with a fusion component to promote fusion of the joint, or coupling the first and second components together using an arthroplasty component to promote arthroplasty of the joint,
   wherein the generally cylindrical solid body of the first component is adapted to be selectively laced within a hollow interior re ion of the second component; and
   engaging the first component to the first bone portion using external threading disposed on the first component.

12. The method of claim 11 wherein a portion of the external threading of the first component is adapted to be engaged with a portion of internal threading of the second component.

13. The method of claim 12 further comprising:
   providing a recess in the proximal end of the first component; and
   providing a fusion component having a first portion comprising a substantially cylindrical body comprising external threading configured to mate with the internal threading of the second component, and further comprising a second portion comprising external threading configured to mate with internal threading of the recess in the proximal end of the first component to promote fusion of the joint.

14. The method of claim 12 further comprising:
   providing a recess in the proximal end of the first component; and
   providing an arthroplasty component having a first portion comprising a substantially cylindrical body comprising external threading configured to mate with the internal threading of the second component, and further comprising a second portion comprising a protrusion configured to rotatably engage the recess of the first component to promote arthroplasty of the joint.

15. Apparatus suitable for treating a medical condition, the apparatus comprising:
   a first component having proximal and distal ends and a generally cylindrical solid body that is engaged with a first bone portion at a joint; and
   a second component having proximal and distal ends, the second component comprising a generally cylindrical body having a hollow interior region, wherein the generally cylindrical solid body of the first component is adapted to be selectively placed within the hollow interior region of the second component, and the second component is adapted to be engaged with a second bone portion at the joint,
   wherein the first component and the second component are configured to be coupled together in a first configuration to promote fusion of the joint, and the first component and the second component are further configured to be coupled together in a second configuration to promote arthroplasty of the joint,
   wherein the proximal end of the first component further comprises a recess; and
   a fusion component having a first portion comprising a substantially cylindrical body having external threading configured to mate with internal threading of the second component, and further comprising a second portion comprising external threading configured to mate with internal threading of the recess of the first component to promote fusion of the joint.

16. Apparatus suitable for treating a medical condition, the apparatus comprising:
   a first component having proximal and distal ends and a generally cylindrical solid body that is engaged with a first bone portion at a joint; and
   a second component having proximal and distal ends, the second component comprising a generally cylindrical body having a hollow interior region, wherein the generally cylindrical solid body of the first component is adapted to be selectively placed within the hollow interior region of the second component, and the second component is adapted to be engaged with a second bone portion at the joint,
   wherein the first component and the second component are configured to be coupled together in a first configuration to promote fusion of the joint, and the first component and the second component are further configured to be coupled together in a second configuration to promote arthroplasty of the joint,
   wherein the proximal end of the first component further comprises a recess; and
   an arthroplasty component having a first portion comprising a substantially cylindrical body comprising external threading configured to mate with internal threading of the second component, and further comprising a second portion comprising a protrusion configured to rotatably engage the recess of the first component to promote arthroplasty of the joint.

* * * * *

UNITED STATES PATENT AND TRADEMARK OFFICE
CERTIFICATE OF CORRECTION

PATENT NO. : 8,454,614 B2
APPLICATION NO. : 13/075984
DATED : June 4, 2013
INVENTOR(S) : Thomas F. Roush It is certified that error appears in the above-identified patent and that said Letters Patent is hereby corrected as shown below:

In the Claims

In column 13, claim 11, line 23, after "be selectively" replace "laced" with --placed--.

In column 13, claim 11, line 24, after "hollow interior" replace "re ion" with --region--.

Signed and Sealed this
Third Day of September, 2013

Teresa Stanek Rea
*Acting Director of the United States Patent and Trademark Office*